(12) United States Patent
Lenna et al.

(10) Patent No.: US 10,189,765 B2
(45) Date of Patent: Jan. 29, 2019

(54) PROCESS FOR THE PREPARATION OF 17β-HYDROXY-DES-A-ANDROST-9,10-EN-5-ONE

(71) Applicant: INDUSTRIALE CHIMICA S.R.L., Milan (IT)

(72) Inventors: Roberto Lenna, S. Giorgio su Legnano (IT); Roberto Di Brisco, Trecate (IT)

(73) Assignee: INDUSTRIALE CHIMICA S.R.L., Milan (IT)

( * ) Notice: Subject to any disclaimer, the term of this patent is extended or adjusted under 35 U.S.C. 154(b) by 0 days.

(21) Appl. No.: 15/771,436

(22) PCT Filed: Oct. 28, 2016

(86) PCT No.: PCT/IB2016/056515
§ 371 (c)(1),
(2) Date: Apr. 27, 2018

(87) PCT Pub. No.: WO2017/072719
PCT Pub. Date: May 4, 2017

(65) Prior Publication Data
US 2018/0339956 A1    Nov. 29, 2018

(30) Foreign Application Priority Data
Oct. 30, 2015 (IT) .................. 102015000067307

(51) Int. Cl.
*C07C 45/00* (2006.01)
*C07C 49/00* (2006.01)
*C07C 49/513* (2006.01)

(52) U.S. Cl.
CPC .......... *C07C 45/004* (2013.01); *C07C 49/513* (2013.01); *C07C 2603/12* (2017.05)

(58) Field of Classification Search
CPC .................... C07C 45/004; C07C 2603/12
See application file for complete search history.

(56) References Cited

U.S. PATENT DOCUMENTS 3,413,314 A    11/1968 Amiard et al.

FOREIGN PATENT DOCUMENTS

WO    WO 2006/013196 A1    2/2006

OTHER PUBLICATIONS

International Search Report and Written Opinion dated Jan. 26, 2017 issued in PCT/IB2016/056515.
G. Saucy et al., "Steroid Total Synthesis , 1-10, Part II; (−)-17.beta.-Hydroxy-des-A-androst-9-en-5-one", Helvetica Chimica Acta (Nov. 1, 1971), vol. 54 , No. 7, pp. 2121-2132.
G. Saucy et al., "Total synthese von Steroiden. 1. Mitteilung. rac-17[beta]-Hydroxydes-A-androst-9-en-5-on", Helvetica Chimica Acta (Nov. 1, 1971), vol. 54, No. 7, pp. 2034-2042.
Andrzej Robert Daniewski et al., "Total Synthesis of [3aS-(3a[alpha],9a[alpha],9b[beta])-3a,4,5,9,9a,9b-Hexahydro-3a,6-dimethyl-1H-benz[e]indene-3,7(2H,8H)-dione and Derivatives, Building Blocks for the Synthesis of Glucocorticoids", Liebigs Annalen der Chemie (Nov. 13, 1989), pp. 1061-1064.

*Primary Examiner* — Sikarl A Witherspoon
(74) *Attorney, Agent, or Firm* — Scully, Scott, Murphy & Presser, P.C.

(57) ABSTRACT

The present invention relates to a new process for the synthesis of 17β-hydroxy-des-A-androst-9,10-en-5-one, the compound of the following formula (1), which can be used as an intermediate in the synthesis of retroprogesterones.

10 Claims, 2 Drawing Sheets

PROCESS FOR THE PREPARATION OF 17β-HYDROXY-DES-A-ANDROST-9,10-EN-5-ONE

FIELD OF THE INVENTION

The present invention relates to the field of processes for the synthesis of active ingredients for pharmaceutical use, and in particular to a process for the industrial-scale preparation of 17β-hydroxy-des-A-androst-9,10-en-5-one, an intermediate useful for the synthesis of retroprogesterones.

BACKGROUND ART

Retroprogesterones are a class of steroids with hormonal activity used in the therapy and treatment of female genital tract dysfunctions and in pregnancy.

The parent compound of the family is retroprogesterone, a compound having a 4-ring steroid structure of the type shown in the following figure:

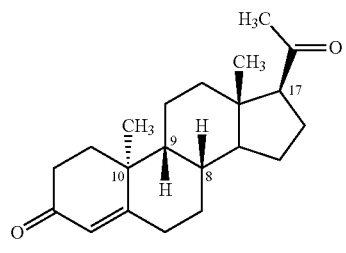

Retroprogesterone wherein the spatial orientation of the hydrogen atoms at positions 8 and 9 is beta while that of methyl at position 10 is alpha; this structure differs from that of progesterone, having the configuration referred to as "natural" shown in the following figure, in the opposite orientation of the hydrogen atom at position 9 (alpha) and the methyl one at position 10 (beta).

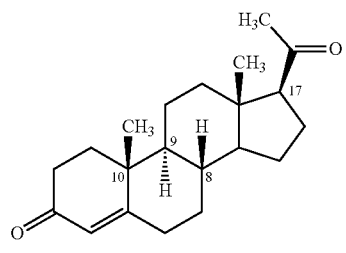

Progesterone

Retroprogesterones useful in the therapeutic field are for example dydrogesterone and trengestone, having the following structural formulas:

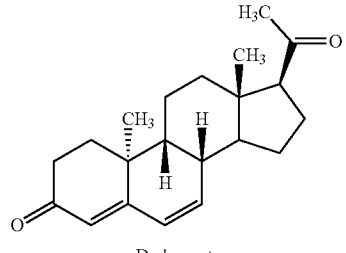

Dydrogesterone

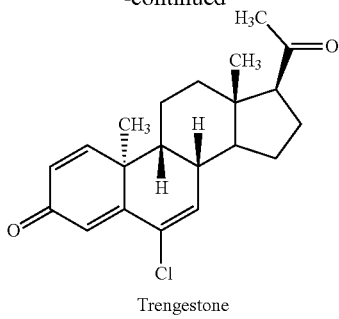

Trengestone

Dydrogesterone has proven effective in treating various conditions associated with a deficiency of progesterone, including infertility due to luteal insufficiency, miscarriage (threatened or recurrent), menstrual disorders, premenstrual syndrome and endometriosis, while trengestone has been employed for the treatment of disorders related to the menstrual cycle.

An intermediate useful in the synthesis of retroprogesterones is the compound of the following formula (1), whose chemical name is 17β-hydroxy-des-A-androst-9,10-en-5-one:

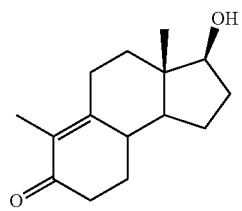

(1)

described in J. Org. Chem, 32, 3008 (1967); the use of the compound as a synthesis precursor of retroprogesterones is reported in J. Org. Chem, 33 (9), 1968.

Compound (1) can be synthesized according to the recipes given in J. Org. Chem, 32, 3008 (1967) starting from the bicyclic intermediate (2) with a series of chemical reactions leading to the racemic mixture of compound (1):

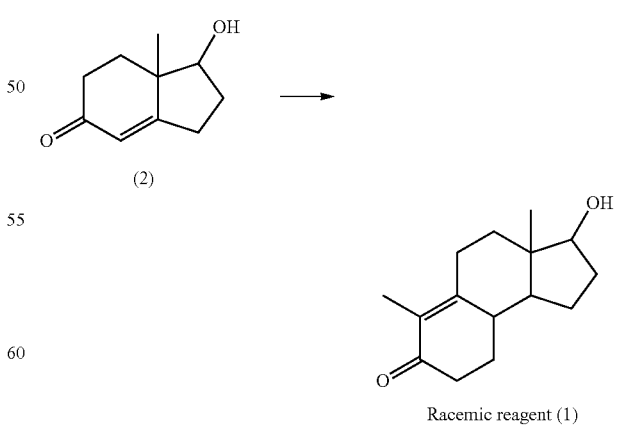

Racemic reagent (1)

Such a racemic mixture cannot be used as such for the preparation of retroprogesterones since it is a mixture of the two optical antipodes.

In the cited article, the authors also report that compound (1) had been previously obtained in the "optically active" form by chemical degradation of testosterone acetate. This method has only scientific value, as it allowed to obtain the optically pure product for the first time but it is not applicable to an industrial production of steroids: in fact, testosterone acetate (4 ring backbone) should be synthesized and the first ring (3 ring backbone) should be degraded and then rebuilt.

The preparation of the compound of formula (1) in optically active form is described in Tetrahedron vol. 24, pp. 2039-2046, 1968; according to the method described, starting from the racemic intermediate (3) and resolving the optical antipodes in the course of the synthesis with brucine salts, compound (1) in optically pure form is obtained:

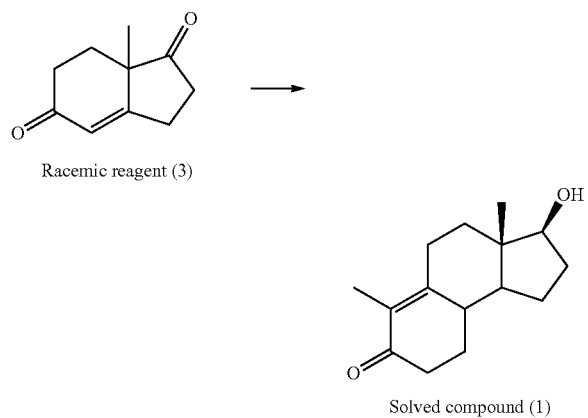

Racemic reagent (3)

Solved compound (1)

Although this synthesis is applicable for the preparation of retroprogesterones, it has the drawback of starting from a racemic reagent; the resolution of a racemate, even in the ideal case of quantitative separation yield, leads to a maximum of 50% yield.

In J MED CHEM 1985, 28, 1796-1803, scheme (I), compounds of general structure (5) are prepared in order to study them and verify their potential pharmacological activity. According to the teachings of the article, these compounds can be prepared starting from precursor (4):

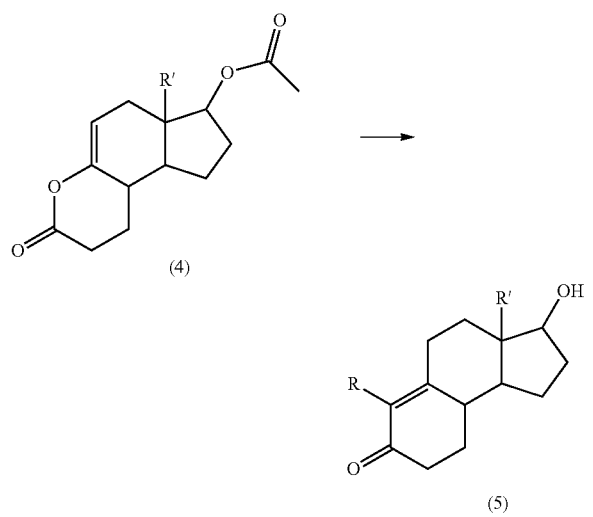

(4)

(5)

In turn, the compounds of general formula (4) can be prepared, as described in U.S. Pat. No. 3,413,314, by total synthesis according to scheme:

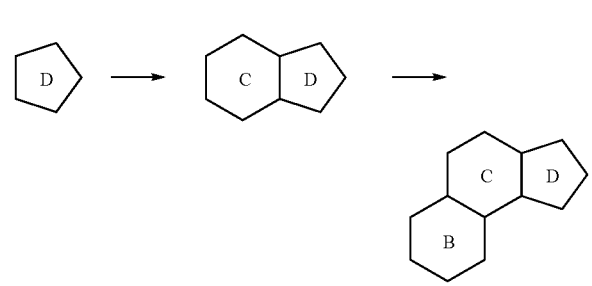

This route of synthesis, however, also has the problem that one of the steps (U.S. Pat. No. 3,413,314, column 2, step d) consists in the separation of the optical antipodes by salification with a chiral amine, with consequent loss of at least half of the starting material.

It is the object of the present invention to provide an improved synthesis route for the preparation of 17β-hydroxy-des-A-androst-9,10-en-5-one, in particular simpler than the prior art processes and industrially applicable.

SUMMARY OF THE INVENTION

This and other objects are achieved by the present invention, which in a first aspect thereof relates to a process for the synthesis of 17β-hydroxy-des-A-androst-9,10-en-5-one, compound (1), comprising the following steps:

a) reaction of compound (4aR,6aS,9aS,9bS)-decahydro-6a-methyl-cyclopenta[f][1]benzopyran-3,7-dione, compound (II), with ethylmagnesium bromide or ethylmagnesium chloride to give the isomer mixture (4S,5R,7aS)-5-hydroxy-7a-methyl-4-(3-oxopentyl)octahydro-1H-inden-1-one and (4S,5S,7aS)-5-hydroxy-7a-methyl-4-(3-oxopentyl)octahydro-1H-inden-1-one, intermediate mixture (III):

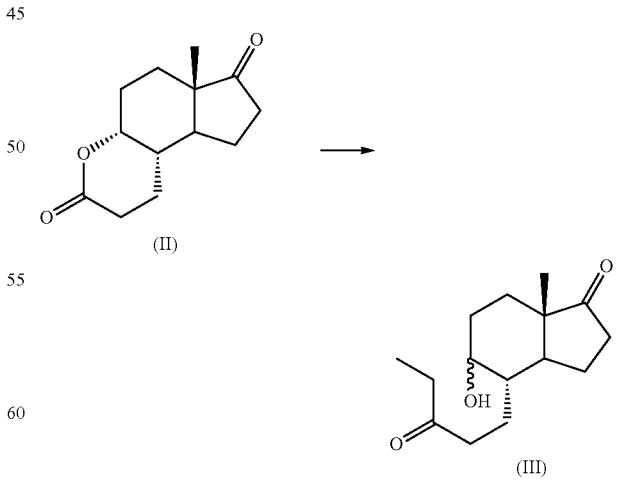

b) oxidation of the intermediate mixture (III) to give (4S,7aS)-7a-methyl-4-(3-oxopentyl)hexahydro-1H-inden-1,5(4H)-dione, intermediate (IV):

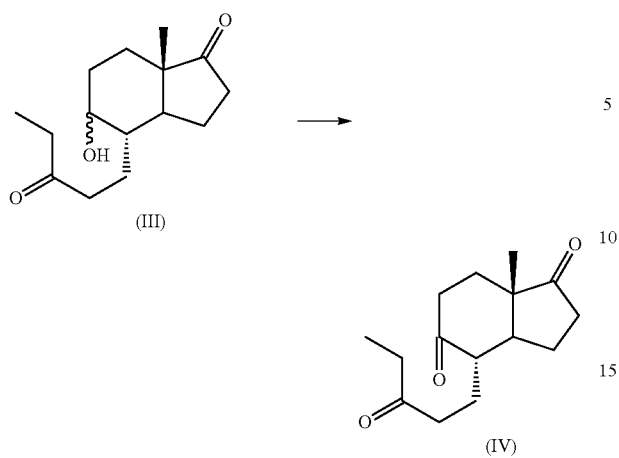

(III)

(IV)

c) cyclization of the intermediate (IV) to give des-A-androst-9,10-en-5,17-dione, intermediate (V):

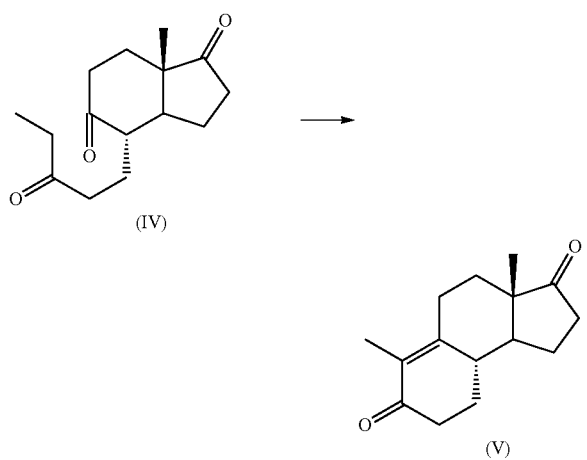

(IV)

(V)

d) reduction of the intermediate (V) to 17β-hydroxy-des-A-androst-9,10-en-5-one (1):

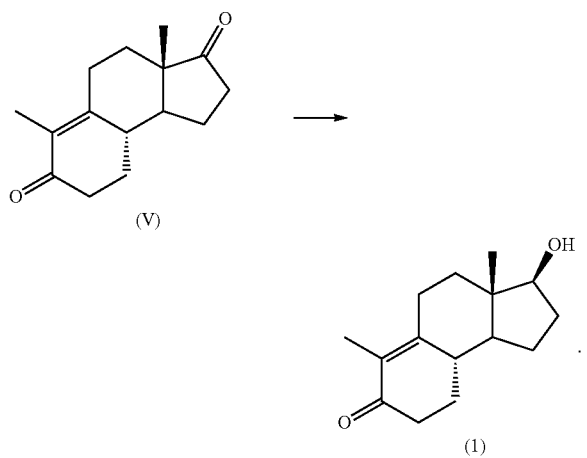

(V)

(1)

A further object of the present invention is the intermediate mixture (III), reaction product of step a) of the process.

DETAILED DESCRIPTION OF THE INVENTION

Figure 1:
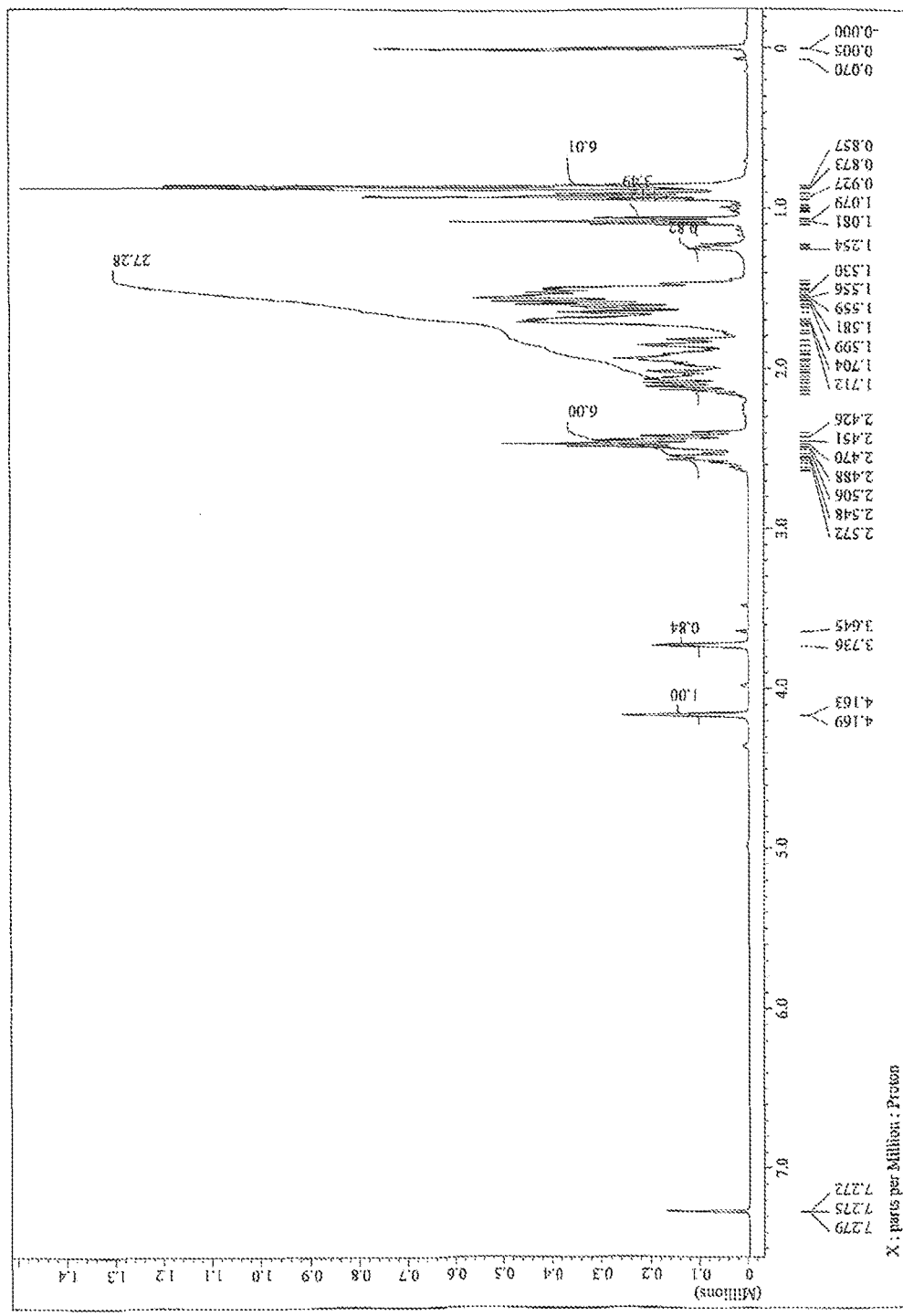
FIG. 1 shows the ¹H-NMR spectrum of the intermediate mixture (III)

In the present description and in the claims, in the event of a discrepancy between the name of a compound and the structure formula given therefor, the latter must be regarded as correct.

The starting material of the process of the invention is compound (II), (4aR,6aS,9aS,9bS)-decahydro-6a-methyl-cyclopenta[f][1]benzopyran-3,7-dione], also known as sitolactone, which name will be adopted hereinafter in the description; the structure of the compound, complete with all relevant stereochemical information, is shown below:

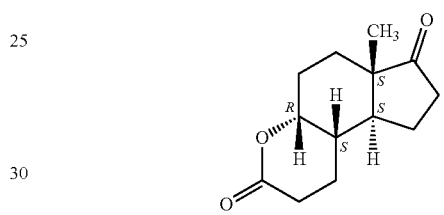

Sitolactone is a commercially available product obtained by microbiological degradation of phytosterols which are waste products from the processing of soy.

The reaction of step a) is conducted in a solvent selected from ethyl ether, isopropyl ether, tetrahydrofuran or methyltetrahydrofuran, either pure or mixed together, operating in an inert atmosphere at a temperature of between −50° C. and 0° C. Preferably, it is conducted in tetrahydrofuran at a temperature of between −45° C. and −20° C., under a mild nitrogen stream.

Sitolactone is reacted with an organometallic reagent (Grignard reagent) wherein the organic part is the ethyl radical, selected from ethylmagnesium chloride and bromide in solution. Preferably, ethylmagnesium bromide in tetrahydrofuran is used, adding this solution portionwise to the reaction mixture.

The amount of reagent to be added and the reaction time are defined by the reaction controls which show the progress thereof, for example TLC or HPLC controls; the intermediate mixture (III) is suitable for subsequent reaction when the sitolactone residue is ≤ 5% of the starting amount. The molar ratio between the organometallic reagent and sitolactone is of between 1 and 2, preferably between 1.05 and 1.25.

The reaction time between the organometallic reagent and sitolactone is generally of between 30 minutes and 2 hours, preferably between 40 and 90 minutes.

The intermediate mixture (III) is formed by the two isomers (4S,5R,7aS)-5-hydroxy-7a-methyl-4-(3-oxopentyl) octahydro-1H-inden-1-one and (4S,5S,7aS)-5-hydroxy-7a-methyl-4-(3-oxopentyl)octahydro-1H-inden-1-one, bearing the OH group at position 5 of the molecule in the two possible orientations, as shown hereinafter:

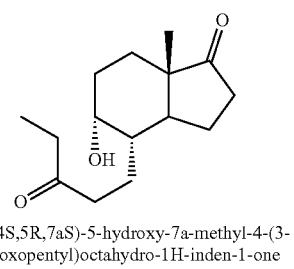

(4S,5R,7aS)-5-hydroxy-7a-methyl-4-(3-oxopentyl)octahydro-1H-inden-1-one

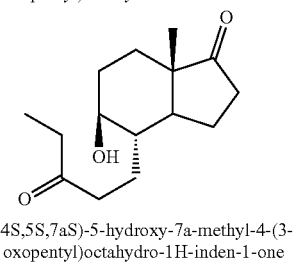

(4S,5S,7aS)-5-hydroxy-7a-methyl-4-(3-oxopentyl)octahydro-1H-inden-1-one

This mixture can be used as such without need for separation of the two components.

Surprisingly, in the reaction conditions, the carbonyl at position 7 of sitolactone reacts only to a negligible extent with the organometallic reagent, making its protection not required.

Step b) reaction is carried out in a solvent selected from ethyl ether, isopropyl ether, tetrahydrofuran, methytetrahydrofuran, acetone, methyl isobutyl ketone, toluene, pure heptane or isomer mixture, cyclohexane, dimethylacetamide, dimethylformamide, chloroform, methylene chloride, dimethylsulfoxide and water, either pure or mixed together.

As the oxidant can be employed trichloroisocyanuric acid (TCCA) in the presence of an organic base such as pyridine or triethylamine; chromium (VI) compounds in the presence of bases such as pyridine, 3,5-dimethylpyrazole or triethylamine, or acids such as sulfuric acid, perchloric acid, acetic acid or hydrochloric acid; 2,2,6,6-tetramethylpiperidine-1-oxyl radical, commonly known as TEMPO, or a derivative thereof such as 4-hydroxy-2,2,6,6-tetramethylpiperidine-1-oxyl radical, 4-methoxy-2,2,6,6-tetramethylpiperidine-1-oxyl radical and 4-(benzoyloxy)-2,2,6,6-tetramethylpiperidine-1-oxyl radical in the presence of a basic aqueous solution and a co-oxidant such as oxygen or sodium or calcium hypochlorite; hypochlorites as main oxidants such as sodium hypochlorite, calcium hypochlorite or tetrabutylammonium hypochlorite; gaseous oxygen or oxygen-nitrogen mixtures in the presence of copper (I) salts such as CuCl; potassium peroxymonosulphate $KHSO_5$, marketed under the name of Oxone® (trademark registered by E.I. du Pont de Nemours and Company); gaseous chlorine dissolved in a halogenated solvent, such as chloroform or carbon tetrachloride; aluminum isopropylate in the presence of a carbonyl compound such as cyclohexanone, benzaldehyde, benzophenone or acetone; dimethyl sulfoxide and an activator such as oxalyl chloride, benzoic anhydride, trifluoroacetic anhydride, $P_2O_5$ and the $SO_3$-pyridine complex in the presence of a base such as triethylamine or diisopropylethylamine; hypervalent iodine compounds such as iodobenzoic acid, also known by the acronym IBX, Dess-Martin periodinane, also known by the acronym DMP, or IBX stabilized with benzoic acid and isophthalic acid, also known by the acronym SIBX Preferably, it is carried out employing trichloroisocyanuric acid (TCCA) as the oxidant in acetone at a temperature of between 5 and 40° C. in the presence of water and pyridine.

The oxidant is added portionwise on the reaction solution; the amount of reagent and the reaction time are defined by the reaction controls which show the progress thereof. The quality of the intermediate (IV) is suitable for subsequent reaction when the unreacted intermediate mixture residue (III) is ≤5% of the starting amount.

In the preferred case of use of TCCA, the required moles of this reagent with respect to the moles of intermediate (III) to be oxidized are in the range between 0.5 and 5, preferably between 0.5 and 1.5; the reaction time, after the addition of TCCA, is of between 30 minutes and 3 h, preferably between 45 minutes and 1.5 h.

The cyclization reaction in step c) can be conducted both on the intermediate (IV) which can be obtained directly from the previous reaction, or on the isolated product.

The reaction is conducted in a solvent selected from ethyl ether, isopropyl ether, tetrahydrofuran, methyltetrahydrofuran, toluene, cyclohexane, n-heptane, heptane isomer mixture, methanol, ethanol, isopropanol, acetic acid, acetonitrile, methylene chloride, water, either pure or mixed together, operating in the presence of basic catalysts such as $NaOCH_3$, $KOCH_3$, KOH, NaOH, $Na_2CO_3$, $K_2CO_3$ or $NaNH_2$, or acid catalysts such as $HClO_4$, $H_2SO_4$ or HCl.

The reaction temperature is between 0 and 40° C., preferably between 10 and 30° C.

The reaction is preferably conducted using KOH as a catalyst in alcoholic or hydroalcoholic solution, preferably methanol and water. Preferably, it is carried out directly on the organic solution of intermediate (IV) obtained in the previous step, without isolation.

The cyclization reaction requires a time of between 1 and 4 h, preferably between 1.5 and 3 h.

The quality of the intermediate (V) is suitable for subsequent reaction when the unreacted intermediate residue (IV) is ≤5% of the starting amount.

The reduction in step d) is carried out using sodium, lithium or potassium metal hydrides, such as sodium borohydride, potassium borohydride, or lithium aluminum hydride; sodium borohydride is preferred.

The reaction temperature is between −10 and 40° C., preferably between 10 and 20° C.

The reaction is conducted in a solvent selected from alcohols, in particular methanol, ethanol, isopropanol or cyclohexanol; or alcohols in admixture with solvents such as ethyl ether, isopropyl ether, tetrahydrofuran, methyltetrahydrofuran, methylene chloride, toluene, cyclohexane, n-heptane, heptane isomer mixture, dimethylformamide or dimethylacetamide. The preferred solvent is methanol.

The hydride is added portionwise on the reaction solution; the amount of reagent and the reaction time are defined by the reaction controls which show the progress thereof.

The moles of sodium borohydride used with respect to the moles of intermediate (IV) are in the range between 0.3 and 1.5, preferably between 0.35 and 0.9; the reaction time is between 1 and 5 h, preferably between 2 and 3.5 h.

The quality of compound (1) is regarded as acceptable when the unreacted intermediate residue (V) is ≤5% of the starting amount.

The invention will be further described by the following examples, given for illustrative, non-limiting purpose.

The reagents used in the examples are of common commercial availability and are used without the need of purification to increase the purity thereof.

Methods and Experimental Conditions
NMR:
NMR spectrometer JEOL 400 YH (400 MHz);
NMR tubes Aldrich® ColorSpec®;
JEOL Delta Software v5.1.1;
Spectra recorded in deuterated chloroform Sigma-Aldrich: Chloroform-d, D 99.8% atomic, containing 0.1% (v/v) tetramethylsilane (TMS) as internal standard; and
Chloroform-d, "100%", D 99.96% atomic, containing 0.03% (v/v) TMS.
MS
HPLC-mass system AB Sciex API 2000 LC/MS/MS;
Samples directly injected and chemically ionized (CI) with formic acid.
DSC
Perkin Elmer Instrument mod. Diamond;
Perkin Elmer Capsules Standard aluminum and lids, code 02190041;
Scanning rate: 10° C./min;
Temperature range: 20° C. to 200° C.
IR
Thermo Scientific Nicolet 6700 spectrometer;
FT-IR spectra recorded in KBr (solid) and smart-iTR-diffuse reflectance (ATR);
Potassium bromide Sigma-Aldrich Code 221864 (for IR analysis).
HPLC
Chromatographic system Agilent model 1200
Detector UV MODEL 1260 DAD VL and Laser Detector 1290 Infinity ELSD
TLC
MERCK: TLC silica gel 60 $F_{254}$ Aluminum sheets 20×20 cm, code 1.0554.0001.
HPTLC
MERCK: HPTLC silica gel 60 $F_{254}$ with concentration zone 10×2.5 cm, code 1.13727.0001.
TLC-RP
MERCK: TLC silica gel 60 RP-18 $F_{254}S$, code 1.15685.0001.
TLC Detectors
Acid solution of cerium phosphomolybdate;
Preparation: 25 g of phosphomolybdic acid hydrate (Aldrich P7390), 10 g of cerium (IV) sulfate hydrate (Aldrich 31606) and 600 mL of water are stirred to dissolution with 60 mL of 95-98% sulfuric acid (Aldrich 258105); this is brought to a final volume of 1000 mL with water; the sheet is then impregnated with the solution, then heated to blue staining.
UV light at 254 and 366 nm.
XRD
Bruker $D_2$Phaser;
X-ray source, copper pipe with λ=1.54184 [Å] powered at 30 kV and 10 mA;
Scanning rate 0.02° 2θ/second
Scanning interval 5° to 35° 2θ;
Assay time 1478 steps in 1704 seconds;
Rotation 10° [1°/min];
SSD160 Detector (1 D mode) with PSD (Position Sensitive Detector) opening of 4.6°.
The following abbreviations are used in the examples:
EtMgBr: ethylmagnesium bromide;
MTBE: methyl t-butyl ether;
TCCA: trichloroisocyanuric acid;
THF: tetrahydrofuran;
Rf: delay factor in thin layer chromatography.

EXAMPLE 1

This example relates to step a) of the process of the invention.

300 g of sitolactone are placed under stirring with 3.6 L of THF under inert atmosphere.

The solution is cooled to a temperature of between −40 and −30° C. (sitolactone partially precipitates again) while stirring.

1.35 L of EtMgBr in THF (1 M solution) are added over 90 minutes and under stirring, keeping the reaction temperature between −40<T<−30° C. (exotherm during the addition).

After the addition, the stirring is continued for 20 minutes keeping the reaction temperature between −40<T<−30° C.

The progress is checked in HPTLC (100% isopropyl acetate eluent) by still detecting about 20% of sitolactone and the formation of a spot at Rf higher than that of sitolactone and some spots of barely detectable intensity.

Additional 300 mL of EtMgBr in THF (1 M solution) are added, keeping the reaction temperature between −40<T<−30° C.

After the addition, the stirring is kept for 20 minutes keeping the reaction temperature between −40<T<−30° C.

The progress is checked in HPTLC (100% isopropyl acetate eluent) by detecting an amount of residual sitolactone of less than 5% with respect to the starting amount, the increase in intensity of the spot at higher Rf and the persistence of some spots of barely detectable intensity.

The reaction solution is then poured slowly and under stirring in 3.4 L of 4% aqueous solution of ammonium chloride precooled at 0<T<5° C. The phases are separated.

The aqueous phase is first extracted with MTBE (3×1.5 L), then the combined organic phases are washed with 1.5 L of NaCl aqueous solution and anhydrified with sodium sulfate. It is filtered and washing the filter with 1 L of MTBE and concentrated to dryness at reduced P, thus obtaining 350.7 g of yellow residue which can be used as such in the next step.

1 g of the residue is purified for analytical purposes by flash chromatography on silica gel, eluting by the isopropyl acetate-heptane isomers 1:1 mixture, and dried under reduced pressure to constant weight (low melting colorless solid).

NMR ($CDCl_3$): the sample is confirmed to be a 54:46 mixture of the two isomers at the hydroxyl of mixture (III) (broad singlet at 4.166 ppm and broad singlet at 3.736 ppm).

The $^1$H-NMR full spectrum is shown in FIG. 1.

Mass spectrum (CI): [$M^+$+1]=253; [$M^+$+1]−$H_2O$=235; [$M^+$+1]−$2H_2O$=217; [$M^+$+1]−$3H_2O$=199.

FT-IR(ATR): 1735 $cm^{-1}$ and 1702 $cm^{-1}$.

EXAMPLE 2

This example relates to steps b) and c) of the process of the invention.

63.42 g of intermediate mixture (III), obtained as described in the previous example, are dissolved by stirring in 286 mL of acetone under an inert atmosphere.

120 mL of pyridine and 2.95 mL of water are added. The Temperature is adjusted to 20° C.

In another container, a solution is prepared with 29.24 g of TCCA with 95.3 mL of acetone and it is slowly dripped on the intermediate mixture solution (III) while keeping the temperature at <25° C.

At the end of the addition, it is stirred for 1 h (formation of a solid already during the dripping) and mild exotherm; temperature is kept at ≤25° C.

The progress is checked in HPTLC (MTBE/heptane 8:2 eluent) by detecting the complete disappearance of the starting reagent, the formation of a main spot at lower Rf than the starting mixture (III) and some spots with detectable intensity.

The mixture is cooled to T=0° C. and filtered, washing the solid on the filter with 60 mL of acetone. The solution is kept at 0° C. for 1 h, the precipitated solid is filtered again and washed it with 60 mL of acetone.

The organic phase is dripped, while keeping the T≤20° C., in an aqueous solution prepared with 97.3 g of $Na_2CO_3$, 117 g of $Na_2SO_3$ and 672 mL of water.

The resulting suspension is filtered and the solid on the filter is washed with 100 mL of acetone and observing the presence of two phases.

The phases are separated, the organic phase is concentrated to small volume and set aside.

The aqueous phase is extracted with 482 mL of toluene and the organic phase is then added to the organic phase set aside before (organic solution C).

In another container, a solution of 103.5 g of KOH, 92 mL of water and 434 mL of methanol is prepared and it is slowly dripped in the organic solution C obtained before. The mixture is stirred keeping T<25° C. for 1 h and 40 minutes.

The progress is checked in TLC-RP (acetone/water 7:3 eluent) by detecting the full disappearance of intermediate (IV) and the formation of a UV visible spot (main product) and some spots of barely detectable intensity.

The phases are separated and the aqueous phase is extracted with 380 mL of toluene.

The organic phases are combined and they are firstly washed with 160 mL of 10% NaCl aqueous solution and then concentrated under reduced pressure to give 51.34 g of an oily product which, over time, spontaneously crystallizes at room temperature.

The residue is recovered adding a mixture of 100 mL of heptane and 5 mL of MTBE, stirring for 30 minutes and evaporating the solvents under reduced P to dryness.

The solid residue is again recovered adding a mixture of 100 mL of heptane and 5 mL of MTBE and stirring for 30 minutes at room temperature.

The solid is then filtered by Büchner funnel and washed with 20 mL of heptane/MTBE 4:1 mixture pre-cooled to 0° C. The product is dried at 40° C. under reduced P to yield 39.4 g of a yellow solid (intermediate V).

3.28 g of orange oil are obtained from the mother liquors after removal of solvent. The oil has been checked by TLC showing the presence of product and other spots.

Analysis:

$^1$H-NMR (CDCl$_3$): 1.03 ppm, singlet, 3H; 1.41-1.54 ppm, multiplet, 2H; 1.54-1.74 ppm, multiplet, 2H; 1.80-1.82 ppm, 3H, triplet, J=1.83 Hz; 1.92-1.97 ppm, doublet of doublets, 1H; 2.01-2.1 ppm, multiplet, 1H; 2.1-2.4 ppm, multiplet, 4H; 2.4-2.6 ppm, multiplet, 3H; 2.86-2.91 ppm, 1H, doublet of doublets.

$^{13}$C-NMR (CDCl$_3$): 219.6 ppm, 198.65 ppm; 156.92 ppm; 130.89 ppm; 50.56 ppm; 47.08 ppm; 38.32 ppm; 36.89 ppm; 35.85 ppm; 30.61 ppm; 26.43 ppm; 21.98 ppm; 12.99 ppm; 11.21 ppm.

Mass spectrum (CI): [M$^+$+1]=233.

FT-IR(KBr): 1735 cm$^{-1}$; 1652 cm$^{-1}$; 1604 cm$^{-1}$.

The DRX spectrum shows the presence of both a crystalline phase (main peaks at values 11.178°, 11.435°, 14.501°, 16.332°, 18.671°, 19.579°, 21.553°, 28.738° of angle 2θ) and of amorphous product.

DSC: transition start at 121° C. and peak at 124° C.

EXAMPLE 3

This example relates to step b) of the process of the invention.

The procedure of the previous example is repeated up to obtaining the organic solution C, which in this case is evaporated (liquid residue).

A sample is purified for analytical purposes by flash chromatography on silica gel, eluting with the isopropyl acetate-heptane isomers 1:1 mixture, and dried under reduced pressure to constant weight (a yellow oil is obtained, intermediate IV).

$^1$H-NMR (CDCl$_3$): 1.04-1.08 ppm, 3H, doublet of triplet, J=7.8 Hz; 1.17 ppm, 3H, singlet; 1.6-1.86 ppm, 5H, multiplet; 1.96-2.12 ppm, 2H, multiplet; 2.18-2.28 ppm, 1H, multiplet; 2.38-2.72 ppm, 8H, multiplet.

$^{13}$C-NMR (CDCl$_3$): 218.1 ppm, 211.54 ppm; 211.102 ppm; 49.59 ppm; 49.14 ppm; 47.59 ppm; 39.84 ppm; 37.54 ppm; 36.19 ppm; 35.99 ppm; 30.51 ppm; 22.36 ppm; 20.28 ppm; 13.62 ppm; 7.89 ppm.

Mass spectrum (CI): [M$^+$+1]=251.

FT-IR (ATR): 1730 cm$^{-1}$

EXAMPLE 4

This example relates to step b) of the process of the invention.

500 mg of intermediate (III) are dissolved at 20° C. in 38 mL of acetone.

1 mL of Jones reagent is added under stirring over 50' keeping the reaction temperature between 15 and 25° C. Jones reagent was prepared in advance by dissolving 27 g of chromic anhydride (Cr$^{VI}$O$_3$) in 100 mL of water then adding 23 mL 98% sulfuric acid.

At the end of the addition, the mixture is stirred for 10', then the completion of the reaction is checked by TLC (MTBE/n-heptane 8:2 eluent).

20 mL of MTBE and 40 mL of 5% NaHCO$_3$ aqueous solution are added to the reaction mixture.

The solid is filtered and washed with 10 mL of MTBE.

The phases are separated and the organic phase is washed with 20 mL of 5% NaHCO$_3$ aqueous solution and with 20 mL of saturated aqueous solution of NaCl.

The organic phase is concentrated under reduced P to yield 370 mg of intermediate (IV).

EXAMPLE 5

This example relates to step b) of the process of the invention.

100 mg of intermediate (III) are dissolved at 20° C. in 5 mL of dichloromethane.

205 mg of Dess-Martin periodinane are portionwise added under stirring over 2.5 h keeping the reaction temperature between 15 and 25° C.

The end of the reaction (residue of intermediate (III) of less than 5% of the starting amount) is checked by TLC (MTBE/n-heptane 82 eluent).

The reaction suspension is filtered and the solid washed with 5 mL of dichloromethane.

The organic phase is concentrated under reduced P and it is chromatographed on silica gel (MTBE/n-heptane 82 eluent) to yield, after removal of the solvent, 60 mg of intermediate (IV).

EXAMPLE 6

This example relates to step d) of the process of the invention.

5 g of intermediate (V), obtained as described in example 2, are dissolved by stirring in 50 mL of methanol at room temperature.

The solution is cooled to T<15° C. and, without ever exceeding this temperature, 204 mg of NaBH$_4$ are added under stirring in 4 portions over 20 minutes.

The mixture is stirred for 30 minutes at 10<T<15° C. and then, the progress is checked in HPTLC (heptane/isopropyl acetate 1:1 eluent) by detecting the formation of a main spot at lower Rf than the intermediate (V), the presence of intermediate (V) and some spots with barely detectable intensity.

The reaction is kept under stirring at 10<T<15° C., adding 50, 20 and 10 mg of NaBH$_4$, respectively, at 30 minute intervals.

The progress of the reaction is checked after each addition by HPTLC as described above. The reaction, checked 30' after the last addition, is deemed as completed.

It is cooled to 0<T<5° C. and, while under stirring, 100 mL of water are added.

It is stirred at 0<T<5° C. for 1 h and the precipitated solid is filtered by Büchner funnel.

After drying under reduced P to constant weight, 4.2 g of compound (1) are obtained as a yellow solid, containing less than 5% of unreacted intermediate (V).

EXAMPLE 7

This example relates to step d) of the process of the invention.

294 g of intermediate (V), obtained as described in example 2, are suspended in 2.5 mL of methanol and stirred for 30' at room temperature (incomplete dissolution).

The solution is cooled to T<15° C. and, without ever exceeding this temperature, a total of 18 g of NaBH$_4$ are added in 10 portions over 160 minutes, checking the progress of the reaction in HPTLC (heptane/isopropyl acetate 1:1 eluent).

At the end of the reaction, it is cooled to 0<T<5° C. while under stirring, 5 L of water are added.

It is stirred at 0<T<5° C. for 1 h and the precipitated solid is filtered by Büchner funnel washing it with water (600 mL).

After drying at 45° C. under reduced P to constant weight, 241 g of compound (1) are obtained (yellow solid), containing less than 5% of unreacted intermediate (V).

A sample of the product thus obtained is purified for analytical purposes by flash chromatography on silica gel, eluting with the heptane isomers:isopropyl acetate 60:40 mixture.

The product has been recovered by evaporation of the eluting solvent and then it was suspended in MTBE at 0<T<5° C. for 30 minutes.

After filtration and drying (T=45° C., P<1 atm) at constant weight, a white solid is obtained.

$^1$H-NMR (CDCl$_3$): 0.91 ppm, 3H, singlet; 1.11-1.72 ppm, 7H, multiplet; 1.79-1.80 ppm, 3H, triplet J=1.6 Hz, J=2 Hz; 1.9-2.05 ppm, 2H, multiplet; 2.08-2.2 ppm, 1H, multiplet; 2.2-2.37 ppm, 3H, multiplet; 2.45-2.54 ppm, 1H, doublet of triplet; 2.79-2.84 ppm, 1H, doublet of doublet; 3.68-3.72 ppm, 1H, triplet, J=8.8 Hz.

$^{13}$C-NMR (CDCl$_3$): 199.16 ppm, 158.59 ppm; 130.10 ppm; 81.28 ppm; 50.48 ppm; 42.44 ppm; 39 ppm; 37.1 ppm; 35.7 ppm; 30.5 ppm; 27.04 ppm; 27 ppm; 23.5 ppm; 11.1 ppm; 10.3 ppm.

Mass spectrum (CI): [M$^+$+1]=235.

FT-IR(KBr): 3451 cm$^{-1}$, 1647 cm$^{-1}$, 1604 cm$^{-1}$

The DRX spectrum shows the presence of a crystalline phase with characteristic peaks at values 11.482°, 16.958°, 17.899°, 18.483°, 19.401° and 24.583° of angle 2θ.

Figure 2:
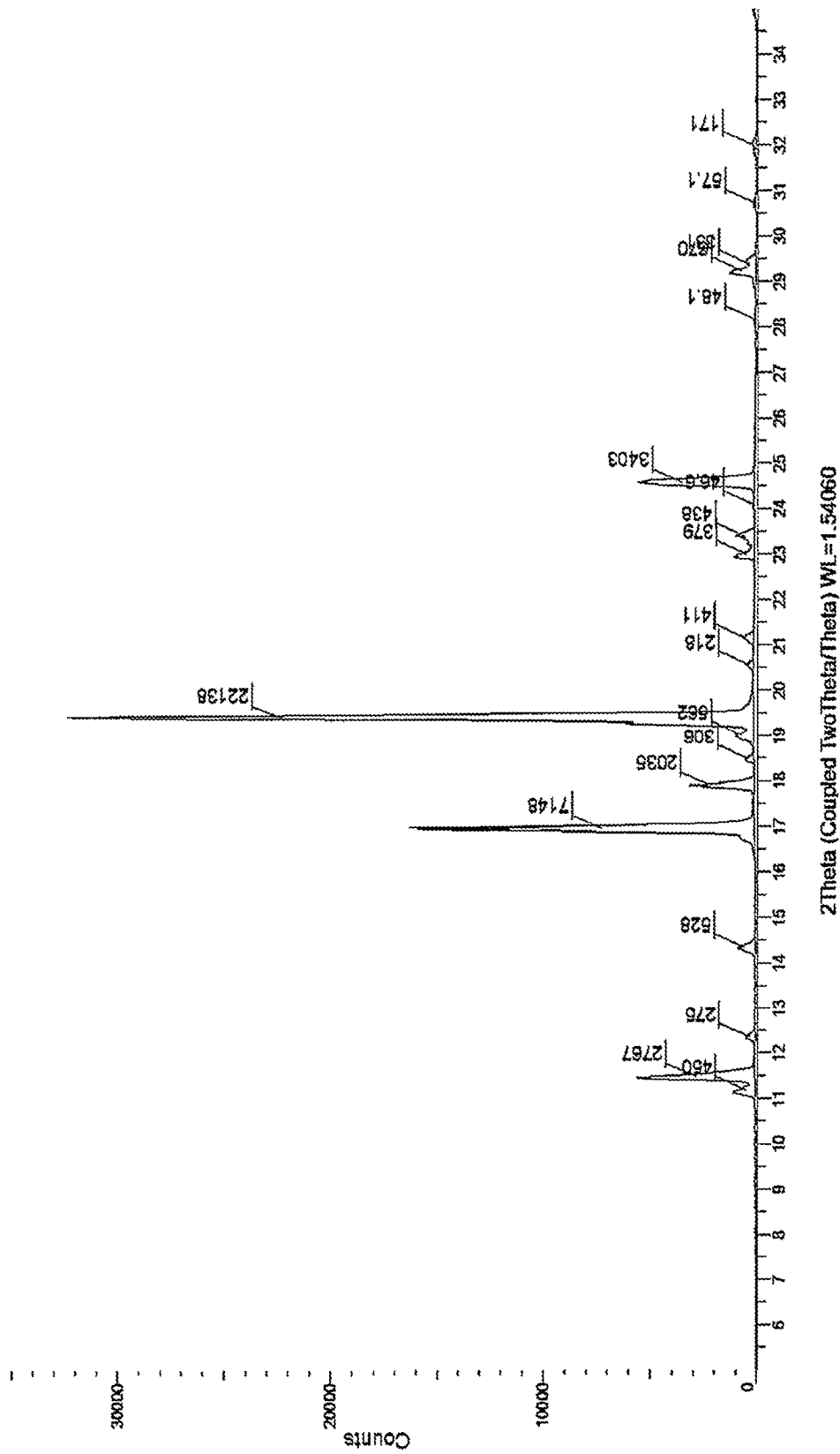
FIG. 2 shows the XRD diffraction pattern of compound (1) obtained according to the invention.

The full diffraction pattern is shown in FIG. 2.

DSC: transition start at 167.5° C., peak at 169.5° C.

$[\alpha]^{25}_D$=−37.5° (1% CH$_3$Cl).

The invention claimed is:

1. A process for the synthesis of 17β-hydroxy-des-A-androst-9,10-en-5-one, compound (1), comprising the following steps:

a) reaction of compound (4aR,6aS,9aS,9bS)-decahydro-6a-methyl-cyclopenta[f][1]benzopyran-3,7-dione, compound (II), with ethylmagnesium bromide or ethylmagnesium chloride to give the mixture of isomers (4S,5R,7aS)-5-hydroxy-7a-methyl-4-(3-oxopentyl)octahydro-1H-inden-1-one and (4S,5S,7aS)-5-hydroxy-7a-methyl-4-(3-oxopentyl)octahydro-1H-inden-1-one, intermediate mixture (III):

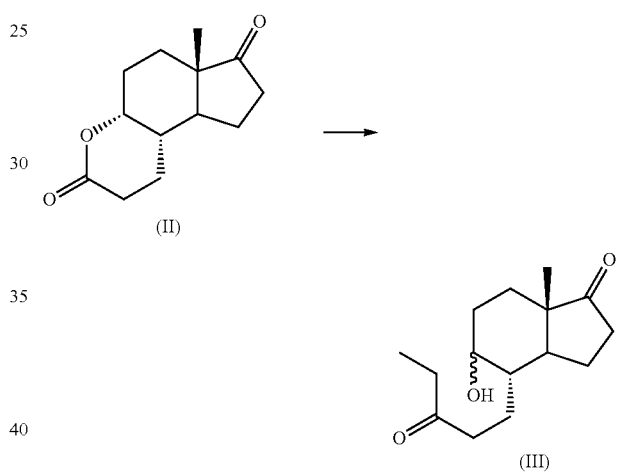

b) oxidation of the intermediate mixture (III) to give (4S,7aS)-7a-methyl-4-(3-oxopentyl)hexahydro-1H-inden-1,5(4H)-dione, intermediate (IV):

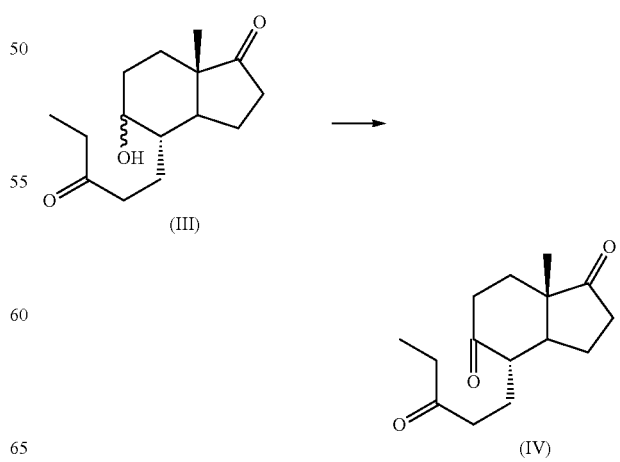

c) cyclization of the intermediate (IV) to give des-A-androst-9,10-en-5,17-dione, intermediate (V):

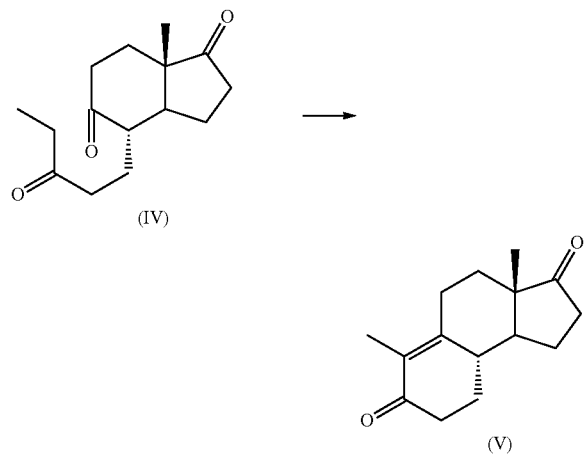

d) reduction of the intermediate (V) to 17β-hydroxy-des-A-androst-9,10-en-5-one, compound (1):

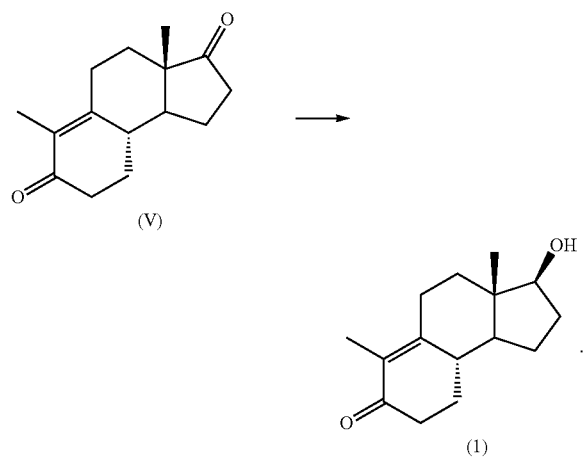

2. The process according to claim 1, in which step a) is carried out in a solvent selected among ethyl ether, isopropyl ether, tetrahydrofuran, methyltetrahydrofuran or mixtures thereof, in an inert atmosphere and at a temperature between −50° C. and 0° C.

3. The process according to claim 1, wherein in step a) the molar ratio between ethylmagnesium bromide or ethylmagnesium chloride and compound (II) is between 1 and 2.

4. The process according to claim 3, wherein said ratio is comprised between 1.05 and 1.25.

5. The process according to claim 1, in which step b) is carried out in a solvent selected among ethyl ether, isopropyl ether, tetrahydrofuran, methyltetrahydrofuran, acetone, methyl isobutyl ketone, toluene, pure heptane or isomer mixture, cyclohexane, dimethylacetamide, dimethylformamide, chloroform, methylene chloride, dimethylsulfoxide, water and mixtures thereof.

6. The process according to claim 1, wherein in step b) as the oxidant it is employed: trichloroisocyanuric acid (TCCA) in the presence of an organic base; compounds of chromium (VI) in the presence of bases or acids; 2,2,6,6-tetramethylpiperidine-1-oxyl radical or a derivative thereof in the presence of a basic aqueous solution and a co-oxidant selected among oxygen and sodium hypochlorite or calcium hypochlorite; sodium hypochlorite, calcium hypochlorite or tetrabutylammonium hypochlorite; gaseous oxygen or oxygen-nitrogen mixtures in the presence of copper (I) salts; potassium peroxymonosulphate $KHSO_5$; gaseous chlorine dissolved in a halogenated solvent; aluminum isopropylate in the presence of a carbonyl compound; dimethyl sulfoxide and an activator selected from oxalyl chloride, benzoic anhydride, trifluoroacetic anhydride, $P_2O_5$ and the $SO_3$-pyridine complex in the presence of a base; an ipervalent iodine compound selected from Dess-Martin periodinane and iodobenzoic acid possibly stabilized with benzoic acid and isophthalic acid.

7. The process according to claim 1 in which step b) is carried out by employing 0.5 to 5 moles of trichloroisocyanuric acid (TCCA) in acetone per mole of intermediate mixture (III) at a temperature between 5 and 40° C.

8. The process according to claim 1 in which step c) is carried out in a solvent selected among ethyl ether, isopropyl ether, tetrahydrofuran, methyltetrahydrofuran, toluene, cyclohexane, n-heptane, heptane isomer mixture, methanol, ethanol, isopropanol, acetic acid, acetonitrile, methylene chloride, water and mixtures thereof, in the presence of a basic or acid catalyst, at a temperature between 0 and 40° C.

9. The process according to claim 1, in which step d) is carried out with a metal hydride at a temperature between −10 and 40° C. in a solvent selected from alcohols or a mixture of an alcohol and a second solvent selected from ethyl ether, isopropyl ether, tetrahydrofuran, methyltetrahydrofuran, methylene chloride, toluene, cyclohexane, n-heptane, heptane isomer mixture, dimethylformamide and dimethylacetamide.

10. A mixture (III) of the isomers (4S,5R,7aS)-5-hydroxy-7a-methyl-4-(3-oxopentyl)octahydro-1H-inden-1-one and (4S,5S,7aS)-5-hydroxy-7a-methyl-4-(3-oxopentyl)octahydro-1H-inden-1-one:

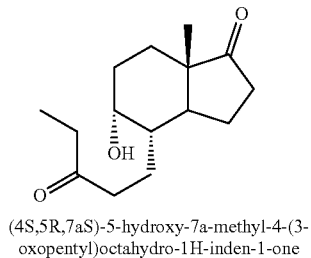

(4S,5R,7aS)-5-hydroxy-7a-methyl-4-(3-oxopentyl)octahydro-1H-inden-1-one

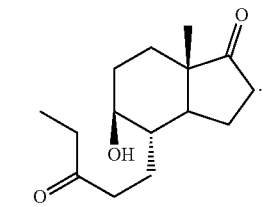

(4S,5S,7aS)-5-hydroxy-7a-methyl-4-(3-oxopentyl)octahydro-1H-inden-1-one

* * * * *